United States Patent [19]

Dürckheimer et al.

[11] Patent Number: 4,609,653

[45] Date of Patent: Sep. 2, 1986

[54] CRYSTALLINE CEPHEM-ACID ADDITION SALTS AND PROCESSES FOR THEIR PREPARATION

[75] Inventors: Walter Dürckheimer, Hattersheim am Main; Rudolf Lattrell, Königstein, both of Fed. Rep. of Germany

[73] Assignee: Hoechst Aktiengesellschaft, Fed. Rep. of Germany

[21] Appl. No.: 565,867

[22] Filed: Dec. 27, 1983

[30] Foreign Application Priority Data

Dec. 28, 1982 [DE] Fed. Rep. of Germany ....... 3248281

[51] Int. Cl.$^4$ ................... A61K 31/545; C07D 501/40
[52] U.S. Cl. ..................................... 514/202; 540/222
[58] Field of Search .......................... 544/22; 424/246; 514/202

[56] References Cited

FOREIGN PATENT DOCUMENTS 62321 10/1982 European Pat. Off. .
2098216 11/1982 United Kingdom .

OTHER PUBLICATIONS

Merck Index 9th ed. 1976, pp. 1932 & 1933.

Primary Examiner—Donald G. Daus
Assistant Examiner—Robert Benson
Attorney, Agent, or Firm—Finnegan, Henderson, Farabow, Garrett & Dunner

[57] ABSTRACT

Crystalline cephem-acid addition salts of the formula

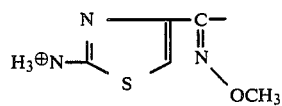

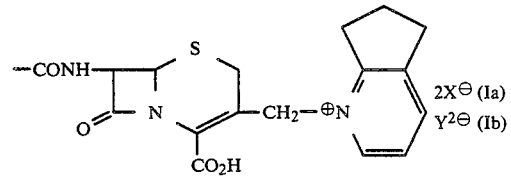

and their hydrates, processes for the preparation of the acid addition salts, pharmaceutical products containing these compounds and processes for their preparation, and the use of the compounds for combating bacterial infections.

3 Claims, No Drawings

CRYSTALLINE CEPHEM-ACID ADDITION SALTS AND PROCESSES FOR THEIR PREPARATION

The invention relates to crystalline acid addition salts of an antibiotic, of the formula Ia or Ib, and hydrates thereof, and processes for the preparation of these compounds.

$$\text{Structure I}$$

$$2X^{\ominus} \text{ (Ia)}$$
$$Y^{2\ominus} \text{ (Ib)}$$

In the general formula I, $X^{\ominus}$ denotes the anion of a monobasic acid and $Y^{2\ominus}$ denotes the anion of a dibasic acid, it being possible for X and Y to be inorganic or organic anions.

Examples of inorganic anions $X^{\ominus}$ and $Y^{2\ominus}$ are $Cl^{\ominus}$, $Br^{\ominus}$, $I^{\ominus}$, $F^{\ominus}$, $NO_3^{\ominus}$, $ClO_4^{\ominus}$, $SCN^{\ominus}$ and $HSO_4^{\ominus}$, and especially physiologically acceptable anions, such as, for example, $Cl^{\ominus}$, $Br^{\ominus}$, $HSO_4^{\ominus}$ and $SO_4^{2\ominus}$. Examples of organic anions $X^{\ominus}$ are anions of aliphatic mono-, di- and tri-carboxylic acids, for example $CH_3CO_2^{\ominus}$, $CF_3CO_2^{\ominus}$ and $CCl_3CO_2^{\ominus}$, and especially anions of physiologically acceptable acids, such as, for example, the monomaleate anion $HOOCCH=CHCO_2^{\ominus}$.

The sulfate, which is distinguished by a very low tendency to incorporate organic solvents into the crystal lattice, is particularly suitable for parenteral use. The dihydriodide is particularly suitable for isolation of the betaine of the formula II from the reaction mixtures.

The processes for the preparation of the acid addition salts of the formulae Ia and Ib comprise (1) reacting a cephem-betaine of the formula II $$\text{Structure II}$$

with monobasic acids of the formula IIIa or dibasic acids of the formula IIIb $$H^{\oplus}X^{\ominus} \qquad \text{IIIa}$$

$$2H^{\oplus}Y^{2\ominus} \qquad \text{IIIb}$$

in which
X and Y have the abovementioned meaning,
or (2) reacting a cephem-betaine of the formula II with acids of the formulae IIIa or IIIb produced in situ from the corresponding salts of the formulae IVa and IVb $$ZX \text{ or } ZX_2 \qquad \text{IVa}$$

$$Z_2Y \text{ or } ZY \qquad \text{IVb}$$

in which

Z denotes a monovalent or divalent metal cation, for example $Na^{\oplus}$, $K^{\oplus}$, $Ag^{\oplus}$ or $Mg^{2\oplus}$, or an ammonium ion, by addition of a strong acid, such as, for example, the mineral acids HCl and $H_2SO_4$, or (3) preparing a water-soluble salt of the formula I, for example a dihydrochloride or sulfate, by process 1 and reacting this with salts of the formulae Iva or Ivb in which $X^{\ominus}$ and $Y^{2\ominus}$ denote anions of a more sparingly water-soluble salt, for example $I^{\ominus}$.

The preparation of the betaine of the formula II on which the salts of the general formula I according to the invention are based is described in German Offenlegungsschrift No. 3,118,732.

In process 1, a monobasic or dibasic acid of the formula IIIa or IIIb is added to a solution of the compound II in water or in a mixture of water and a water-miscible organic solvent, such as, for example, methanol, ethanol, isopropanol, acetone, tetrahydrofuran or acetonitrile. The acids $H^{\oplus}X^{\ominus}$ and $2H^{\oplus}Y^{2\ominus}$ can be added in undiluted form or in solution, for example in water or in the abovementioned water-miscible organic solvents, or in mixtures of water and these solvents.

Formation of the salts of the formulae Ia and Ib is carried out at temperatures between $-20°$ and $+80°$ C., preferably between $-5°$ and $+30°$ C. The salts crystallize spontaneously on standing, with stirring or after seeding or by precipitation with a solvent, such as acetone or ethanol.

At least twice the equimolar amount of the acid of the formula III must be added, but an excess can also be used.

After the acid III has been added, a solution is first formed, which can be filtered. In some cases, it may be advantageous to clarify the solution with active charcoal before filtration.

The process can also be carried out by taking a solution of the acid III and adding the cephem base II directly or as a solution in water.

The starting compound of the formula II can also be liberated from one of its salts by treatment with a basic ion exchanger, for example the solid exchanger Amberlite IRA 93 or the liquid exchanger Amberlite LA-2, in aqueous solution and then converted into an acid addition salt as described above.

In process 2, at least twice the equimolar amount up to a tenfold excess of the salt of the formula IV or Ivb is added to the solution of the compound II and the acid $H^{\oplus}X^{\ominus}$ or $2H^{\oplus}Y^{2\ominus}$ on which the salt is based is liberated by addition of a strong mineral acid, such as, for example, HCl or $H_2SO_4$.

The corresponding sparingly soluble salts can in this manner be prepared with acids, for example, from HI or HSCN formed in situ.

In process 3, a salt of the formula IVa or IVb which is based on an anion which forms a more sparingly soluble acid addition salt with the compound II, for example, the dihydriodide or dihydroperchlorate of the compound II, is added to the solution of a salt Ia or Ib in water. The reaction procedure and crystallization are as described in process 1.

The compounds of the formulae Ia and Ib obtained by the above processes are isolated by, for example, filtration or centrifugation and are advantageously dried with the aid of a dehydrating agent, such as, for example, concentrated sulfuric acid or phosphorus pentoxide, under normal pressure or in vacuo. The compound of the formula I is thereby obtained as the hydrate or in anhydrous form, depending on the drying conditions.

The compounds of the general formula I obtained according to the invention display remarkably good antibacterial activities, both against Gram-positive and against Gram-negative bacterial germs.

The compounds of the formula I also have an unexpectedly good action against penicillinase- and cephalosporinase-forming bacteria. Since they also exhibit favorable toxicological and pharmacological properties, they are valuable chemotherapeutics.

The invention thus also relates to medicament products for the treatment of microbial infections, which contain one or more of the compounds according to the invention, in particular the physiologically acceptable acid addition salts.

The products according to the invention can also be used in combination with other active compounds, for example from the penicillin, cephalosporin or aminoglycoside series.

The compounds of the general formula I can be administered subcutaneously, intramuscularly, intraarterially or intravenously.

Medicament products which contain one or more compounds of the general formula I as the active compound can be prepared by mixing the compounds of the formula I with one or more pharmacologically acceptable carriers or diluents, such as, for example, buffer substances, and converting the mixture into a formulation form suitable for parenteral administration.

Examples of diluents which may be mentioned are polyglycols, ethanol and water. Examples of buffer substances are organic compounds, such as, for example, N',N'-dibenzylethylenediamine, diethanolamine, ethylenediamine, N-methylglucamine, N-benzylphenethylamine, diethylamine and tris(hydroxymethyl)aminomethane, or inorganic compounds, such as, for example, phosphate buffers, sodium bicarbonate and sodium carbonate. Suspensions or solutions in water, with or without buffer substances, are preferably used for parenteral administration.

Suitable doses of the compounds of the general formula I are about 0.4 to 20 g/day, preferably 0.5 to 4 g/day, for an adult weighing about 60 kg.

Single or, generally, multiple doses can be administered, and the single dose can contain the active compound in an amount of about 50 to 1,000 mg, preferably about 100 to 500 mg.

It was to be expected that salt formation would be effected with one mole of acid, on the basis of the monobasic function of the starting material. It was therefore surprising that, according to the invention, acid addition salt formation takes place only with 2 moles of said and crystalline salts with increased stability are formed.

The following embodiment examples of acid addition salts of the compound II, i.e. 1-[[(6R,7R)-7-[2-(2-amino-4-thiazolyl)-glyoxylamido]-2-carboxy-8-oxo-5-thia-1-azabicyclo[4.2.0]oct-2-en-3-yl]methyl]-6,7-dihydro-5H-cyclopenta[b]pyridinium hydroxide, inner salt, 7²-(Z)-(O-methyloxime), which can be prepared according to the invention, serve to further illustrate the invention, but do not restrict it thereto.

EXAMPLE 1

Dihydronitrate of the compound II (process 1)

10.3 g (0.02 mole) of the compound II are dissolved in 80 ml of water at room temperature, and 100 ml of 0.85N nitric acid are added all at once, whilst shaking. The insoluble constituents are immediately filtered off with suction and washed with 10 ml of 0.85N nitric acid. The dihydronitrate crystallizes out of the filtrate within 15 minutes. After the mixture has been left to stand at 5° C. for 2 hours, the crystals are filtered off with suction and washed with 20 ml of 0.85N nitric acid and with three 50 ml portions of diethyl ether. After drying at room temperature in vacuo over $P_2O_5$, 9.8 g (72.5% of theory) of colorless crystals of decomposition point 138°–140° C. are obtained. A further 0.9 g (6.6%) of decomposition point 134° C. can be obtained by concentrating the mother liquor in vacuo.

$C_{22}H_{22}N_6O_5S_2 \times 2HNO_3 \times 2H_2O$ (676.65); Calculated: C 39.05 H 4.17 N 16.56 S 9.48 $H_2O$ 5.32%; Found: C 38.9 H 4.2 N 16.6 S 9.4 $H_2O$ 5.3%.

1H-NMR ($CF_3CO_2D$): $\delta$=2.30–2.85 (m,2H,cyclopentene-H); 3.15–4.05 (m,6H,4-cyclopentene-H and $SCH_2$); 4.30 (s,3H,$OCH_3$); 5.20–6.35 (m,4H,$CH_2$Py and 2 lactam-H); 7.65–8.72 (m,3H,Py); and 9.22 ppm (s,1H,thiazole).

EXAMPLE 2

Dihydroperchlorate of the compound II (process 1)

3 ml of 1N $HClO_4$ are added to a solution of 0.51 g (1 mmole) of the compound II in 5 ml of water. A precipitate forms immediately and is filtered off with suction, washed with five 1 ml portions of ice-water and dried over $P_2O_5$ in vacuo.

Yield: 0.56 g (78.2% of theory) of colorless crystals of decomposition point 177°–179° C.

$C_{22}H_{22}N_6O_5S_2 \times 2HClO_4 \times H_2O$ (733.54); Calculated: C 36.02 H 3.57 Cl 9.66 N 11.46 S 8.74 $H_2O$ 2.45%; Found: C 35.9 H 3.7 Cl 9.5 N 11.5 S 8.8 $H_2O$ 1.7%.

$^1$H-NMR ($CF_3CO_2D$): $\delta$=2.25–2.85 (m,2H,cyclopentene-H); 3.20–4.06 (m,6H,4 cyclopentene-H and $SCH_2$); 4.28 (s,3H,$OCH_3$); 5.25–6.25 (m,4H,$CH_2$Py and 2 lactam-H); 7.42 (s,1H,thiazole); 7.65–8.75 ppm (m,3H,Py)

EXAMPLE 3

The dihydrotetrafluoborate of the compound II (process 1)

3 ml of 1N $HBF_4$ are added to a solution of 0.51 g (1 mmole) of the compound II in 4 ml of water. The precipitate formed is filtered off with suction, after 3 hours at 0°, and is washed with four 0.5 ml portions of ice-water and dried over $P_2O_5$. Yield: 0.43 g (62.3% of theory) of colorless crystals which decompose from 148° C.

$C_{22}H_{22}N_6O_5S_2 \times 2HBF_4 \times H_2O$ (708.25); Calculated: C 37.31 H 3.70 F 21.46 N 11.87 S 9.05 $H_2O$ 2.45%; Found: C 37.9 H 3.7 F 20.5 N 12.0 S 9.7 $H_2O$ 2.8%.

$^1$H-NMR ($CF_3CO_2D$): $\delta$=2.30–2.80 (m,2H,cyclopentene-H); 3.15–4.03 (m,6H,4-cyclopentene-H and $SCH_2$); 4.28 (s,3H,$OCH_3$); 5.28–6.25 (m,4H,$CH_2$Py and 2 lactam-H); 7.42 (s,1H,thiazole and 7.65–8.70 ppm (m,3H,Py).

EXAMPLE 4

The dihydriodide of the compound II (process 1)

5.15 g (0.01 mole) of the compound II are dissolved in 80 ml of water, and 25 ml of 1N aqueous hydriodic acid are added. After a short time, a colorless precipitate forms. After 1 hour at 20°, the precipitate is filtered off with suction and washed with two 20 ml portions of cold water. After drying over $P_2O_5$ in vacuo, 6.4 g (83% of theory) of colorless crystals of decomposition point 182°–184° C. are obtained.

$C_{22}H_{22}N_6O_5S_2 \times 2HI$ (770.42); Calculated: C 34.30 H 3.14 I 32.94 N 10.91 S 8.32%; Found: C 33.3 H 3.7 I 33.5 N 10.5 S 8.3%.

$^1$H-NMR ($CF_3CO_2D$): $\delta = 2.30$–2.85 (m,2H,cyclopentene-H); 3.10–4.05 (m,6H,4 cyclopentene-H and $SCH_2$); 4.41 (s,3H,$OCH_3$); 5.25–6.20 (m,4H,$CH_2Py$ and 2 lactam-H); 8.11 (s,1H,thiazole); 7.65–8.70 ppm (m,3H,Py)

EXAMPLE 5

The dihydriodide of the compound II (process 2)

0.51 g (1 mmole) of the compound II and 0.66 g (4 mmoles) of KI are dissolved in 10 ml of water. The solution is adjusted to pH 1.0 with 0.5 ml of 5N HCl, while stirring, whereupon a colorless precipitate separates out. After 1 hour at 10° C., the precipitate is filtered off with suction and washed with three 3 ml portions of water. After drying, 0.60 g (78% of theory) of colorless crystals are obtained. The compound is identical in all properties to that described above.

EXAMPLE 6

The dihydriodide of the compound II (process 3)

57.5 g (0.091 mole) of the sulfate of the compound II (Example 8) are dissolved in 1.2 liters of water, and a solution of 55 g (0.35 mole) of KI in 50 ml of water is then added. Undissolved impurities are removed by filtration through a clarifying layer filter (SWK Supra 200, Messrs. Seitz, Kreuznach). The colorless dihydriodide crystallizes out of the clear filtrate. After 1 hour in an ice-bath, the crystals are filtered off with suction and washed free of sulfate with a little ice-water. After drying over $P_2O_5$ in vacuo, 61.4 g (85.4% of theory) are obtained. The compound is identical in all properties to that described in Example 4.

EXAMPLE 7

The dihydrothiocyanate of the compound II (process 2)

0.51 g (1 mmole) of the compound II and 0.39 g (4 mmoles) of KSCN are dissolved in 10 ml of water. After 1 ml of 1N HCl has been added, 0.2 g of animal charcoal is added and the mixture is stirred for 5 minutes and filtered. 2 ml of 1N HCl are added to the filtrate, the mixture is stirred at 10° C. for 2 hours and the precipitate is filtered off with suction and washed with three 2 ml portions of ice-water.

After drying over $P_2O_5$ in vacuo, 0.46 g (71% of theory) of colorless crystals which decompose from 170° C. are obtained.

$C_{22}H_{22}N_6O_5S_2 \times 2HSCN \times H_2O$ (650.77); Calculated: C 44.20 H 4.03 N 17.22 S 19.71 $H_2O$ 2.74%; Found: C 43.7 H 4.2 N 16.8 S 19.3 $H_2O$ 2.3%.

$^1$H-NMR ($CF_3CO_2D$): $\delta = 2.25$–3.85 (m,2H,cyclopentene-H), 3.15–4.03 (m,6H,4 cyclopentene-H and $SCH_2$); 4.38 (0.3H,$OCH_3$); 5.30–6.33 (AB,2H,$CH_2Py$); 5.41 (d,1H,J=5 Hz,C-6-H), 6.12 (d,1H,J=5 Hz,C-7-H); 7.42 (s,1H,thiazole); 7.68–8.70 ppm (m3H,Py).

EXAMPLE 8

The sulfate of the compound II (process 1)

25.7 g (0.05 mole) of the compound II are dissolved in 80 ml of water, and 100 ml of 1N sulfuric acid followed by 250 ml of ethanol are added dropwise at 5° C., while stirring. Small amounts of resinous impurities are filtered off with suction, if necessary, over a clarifying layer filter. The sulfate crystallizes out of the clear filtrate within about 1 hour. After 3 hours, the crystals are filtered off with suction and washed with 40 ml of water:ethanol (1:2) and with two 30 ml portions of ethanol. After drying over sulfuric acid under normal pressure for three days 24.6 g (78% of theory) of colorless crystals of decomposition point 198°–202° C. are obtained.

$C_{22}H_{22}N_6O_5S_2 \times H_2SO_4 \times H_2O$ (630.70); Calculated: C 41.90 H 4.16 N 13.33 S 15.25 $H_2O$ 2.85%; Found: C 41.9 H 4.2 N 13.4 S 15.0 $H_2O$ 2.3%.

$^1$H-NMR ($D_2O$): $\delta = 2.00$–2.60 (m,2H,cyclopentene-H); 3.00–3.70 (m,6H,4 cyclopentene-H and $SCH_2$); 4.03 (s,3H, $OCH_3$); 5.15–5.93 (m,4H,$CH_2Py$ and 2 lactam-H); 7.11 (s,1H,thiazole); 7.66–8.62 ppm (m,3H,Py)

EXAMPLE 9

The sulfate of the compound II (process 1)

33.7 g (0.05 mole) of the dinitrate from Example 1 are suspended in 100 ml of water, a solution of 50 ml of Amberlite LA-2 (Serva 40610) in 200 ml of diethyl ether is added and the mixture is stirred in an ice-bath for 15 minutes. The phases are separated and the aqueous phase is extracted with four 100 ml portions of methylene dichloride. 100 ml of 1N sulfuric acid followed by 350 ml of ethanol are added dropwise to the aqueous phase, with stirring. Small amounts of undissolved resinous constituents are removed by filtration over a clarifying layer. The sulfate crystallizes out of the filtrate. After 2 hours in an ice-bath, the crystals are filtered off with suction, washed with alcohol and dried as above. The yield is 18.9 g (59.9% of theory). The compound is identical in all its properties to that described above.

EXAMPLE 10

The dihydrochloride of the compound II (process 1)

0.51 g (1 mmole) of the compound II are dissolved in 4 ml of 0.5N hydrochloric acid. The solution is freeze-dried and the residue is digested with 8 ml of boiling ethanol. The undissolved resin is decanted off and the solution is left at +3° overnight. The precipitate formed is filtered off with suction, washed with two 1 ml portions of ethanol and dried over $P_2O_5$ in vacuo. Yield: 250 mg (41.3% of theory), product decomposes from 190° C. $C_{22}H_{22}N_6O_5S_2 \times 2HCl \times H_2O$ (605.54); Calculated: C 43.64 H 4.33 Cl 11.71 N 13.88 S 10.59 $H_2O$ 2.98%; Found: C 42.6 H 4.6 Cl 11.9 N 13.5 S 10.3 $H_2O$ 3.9%.

$^1$H-NMR ($CF_3CO_2D$): $\delta = 2.20$–2.85 (m,2H,cyclopentene-H); 3.10–4.02 (m,6H,4 cyclopentene-H and $SCH_2$); 4.26 (s,3H,$OCH_3$); 5.26–6.28 (m,4H,$CH_2Py$ and 2 lactam-H); 7.41 (s,1H,thiazole); 7.68–8.75 ppm (m,3H,Py)

EXAMPLE 11

The dihydrobromide of the compound II (process 1)

0.51 g (1 mmole) of the compound II is dissolved in 4 ml of water, and 5 ml of 1N HBr are added. After the mixture has been left to stand overnight, the precipitate is filtered off with suction and washed with three 0.5 ml portions of ice-water. After drying over $P_2O_5$, 440 mg (63.5% of theory) of colorless crystals of decomposition point 185°–187° C. are obtained.

$C_{22}H_{22}N_6O_5S_2 \times 2HBr \times H_2O$ (694.45); Calculated: C 38.05 H 3.77 Br 23.01 N 12.10 S 9.24 $H_2O$ 2.59%; Found: C 37.7 H 4.2 Br 22.1 N 12.1 S 10.1.

$^1$H-NMR ($CF_3CO_2D$): $\delta = 2.20-2.80$ (m,2H,cyclopentene-H); 3.10–3.85 (m,6H,4 cyclopentene-H and $SCH_2$), 4.25 (s,3H,$OCH_3$); 5.30–6.30 (m,4H,$CH_2Py$ and 2 lactam-H); 8.10 (s,1H,thiazole); 7.65–8.90 ppm (m,3H,Py).

EXAMPLE 12

The dihydromaleate of the compound II (process 1)

3.1 g (6 mmoles) of the compound II and 1.74 g (15 mmoles) of maleic acid are dissolved in 16 ml of water, and 15 ml of acetone are added. The mixture is filtered with suction to remove a slight turbidity and the clear filtrate is left at 3° C. overnight. The precipitate formed is filtered off with suction and washed with two 10 ml portions of acetone:water (2:1). After drying in vacuo over $P_2O_5$ for 2 hours at 60° C., 3.3 g (72% of theory) of colorless crystals of decomposition point 137°–139° C. are obtained.

$C_{22}H_{22}N_6O_5S_2 \times C_8H_8O_8 \times H_2O$ (764.72); Calculated: C 47.11 H 4.22 N 10.99 S 8.39%; Found: C 47.5 H 4.4 N 11.1 S 8.6%.

$^1$H-NMR ($CF_3CO_2D$): $\delta = 2.25-3.85$ (m,2H,cyclopentene-H); 3.15–4.02 (m,6H,4 cyclopentene-H and $SCH_2$); 4.26 (s,3H,$OCH_3$); 5.25–6.10 (AB,2H,$CH_2Py$); 5.42 (d,1H,J=5 Hz,C-6-H); 6.32 (d,1H,J=5 Hz,C-7-H); 6.65 (s,4H,maleic acid); 7.42 (s,1H,thiazole), 7.66–8.68 ppm (m,3H,Py).

EXAMPLE 13

The dihydromaleate of the compound II (process 1)

27 g (0.04 mole) of the dihydronitrate of II are suspended in 80 ml of water, a solution of 45 ml of Amberlite LA-2 (Serva 40610) in 130 ml of methyl isobutyl ketone are added and the mixture is stirred in an icebath for 30 minutes. The phases are separated and the aqueous phase is washed with three 50 ml portions of diethyl ether. 9.3 g (0.08 mole) of maleic acid are dissolved in the aqueous phase, the solution is stirred at 25° C. for 15 minutes and resinous impurities are filtered off. The clear filtrate is cooled for 0°, and precipitation of the dimaleate starts after a short time. After 3 hours at 0°, the precipitate is filtered off with suction, washed with two 10 ml portions of ice-water and dried over $P_2O_5$ in vacuo.

Yield: 18.4 g (60.5% of theory) of decomposition point 136°–138° C.

The compound is identical in all properties to that of Example 12.

We claim:

1. A crystalline cephem-acid addition salt of the formula I or the monohydrate thereof in which
X$^-$ represents a chloride, bromide, iodide, or hydromaleate anion in formula Ia and
Y$^{2-}$ represents a sulfate anion in formula Ib.

2. A dry non-liquid pharmaceutical composition which is effective against bacterial infections, which contains an effective amount of the crystalline cephem compound of the Formula I as defined in claim 1.

3. The use of a crystalline cephem compound of the Formula I as defined in claim 1 for combating bacterial infection.

* * * * *